United States Patent [19]

Barnett, Jr.

[11] Patent Number: 4,975,425

[45] Date of Patent: Dec. 4, 1990

[54] PESTICIDAL AND HERBICIDAL FOAMS

[75] Inventor: Horace G. Barnett, Jr., Kansas City, Mo.

[73] Assignee: Mobay Corporation, Pittsburgh, Pa.

[21] Appl. No.: 324,155

[22] Filed: Mar. 16, 1989

[51] Int. Cl.$^5$ .................. A01N 57/00; A01N 43/48; A01N 43/60; A61K 31/66

[52] U.S. Cl. .................................. 514/119; 71/78; 71/88; 71/92; 71/93; 71/94; 71/95; 71/98; 71/103; 71/110; 71/118; 514/184; 514/212; 514/255; 514/326; 514/383; 514/398; 514/417; 514/471; 514/476; 514/491; 514/600

[58] Field of Search .............. 514/119, 945, 184, 383, 514/255, 326, 422, 212, 227, 471, 476, 491, 398, 417, 600; 252/307; 71/DIG. 1, 78, 92, 93, 88, 94, 95, 98, 103, 110, 118

[56] References Cited

U.S. PATENT DOCUMENTS

| | | | |
|---|---|---|---|
| 3,524,911 | 8/1970 | Leavitt | 424/45 |
| 3,689,245 | 9/1972 | Weldman et al. | 71/65 |
| 3,713,404 | 1/1973 | Lavo et al. | 111/1 |
| 3,810,981 | 5/1974 | Olin | 514/119 |
| 3,922,977 | 12/1975 | Lavo et al. | 111/1 |
| 4,086,331 | 4/1978 | Neumann | 424/45 |
| 4,152,428 | 5/1979 | Salbeck et al. | 514/119 |
| 4,176,176 | 11/1979 | Cella et al. | 424/70 |
| 4,283,395 | 8/1981 | Fancher | 514/119 |

OTHER PUBLICATIONS

Lambou et al., "Whey Solids as Agricultural Foam Stabilizers," Journal of Agr. Chem. vol. 21, No. 2, 1973.
McCall et al., "Influence of Foam Adjuvants on Activity of Selected Herbicides" Weed Science, vol. 22, Issue 4, Jul., 1974.
Material Data Safety Sheets, pp. 1-3, Witco.
Chemical Abstract, vol. 97, No. 7874z, Albanese, "Water Dispersions", 1982.

*Primary Examiner*—Richard L. Raymond
*Assistant Examiner*—Raymond Covington
*Attorney, Agent, or Firm*—Joseph C. Gil; Lyndanne M. Whalen

[57] ABSTRACT

Foam compositions containing a herbicide or pesticide which are readily absorbed systemically by plant life are made by incorporating a gas such as air into a composition made up of an alcohol, a modified coconut acid or a blend of nonionic and anionic surfactants, water and a systemic herbicide or pesticide. These foam compositions are applied directly to plant life such as trees and are absorbed within three minutes, often within one minute.

5 Claims, No Drawings

PESTICIDAL AND HERBICIDAL FOAMS

BACKGROUND OF THE INVENTION

The present invention relates to foam compositions containing a systemic pesticide or herbicide, a process for their production and to a method for applying them.

Agricultural chemicals such as herbicides and pesticides have been applied by a variety of techniques. One technique which has been found to be particularly advantageous is the incorporation of the agricultural chemical into a foam or a foam-forming composition because application in this manner reduces the loss of such chemicals due to wind drift. The application of foams is also more controllable than spraying of liquids and waste due to application in an unintended area is substantially reduced.

It has generally been assumed that long lasting foams are particularly desirable because the insecticide or herbicide would be released at a controlled rate for a prolonged period of time.

A small scale example of such foam compositions is seen in U.S. No. 3,524,911 which teaches aerosol insecticidal compositions. The disclosed compositions are suitable for use on relatively small areas but are impractical for application to large fields of crops.

U.S. No. 3,689,245 discloses agricultural pesticides which are dispersed or dissolved in an aqueous alkali metal silicate foam. These foams are said to expand to a volume of from 3 to 300 times the volume of the liquid in the foam. The alkali metal silicate content of the foam is from 5 to 50% by weight. The pesticide is present in an amount of from 0.1 to 25% by weight of the foam.

U.S. Nos. 3,713,404 and 3,922,977 disclose the use of high expansion foams (i.e., foams which expand the volume of the liquid stream of the foam-providing solution at least 80 fold) as vehicles for applying needs fertilizers and other biological agents such as insecticides and herbicides. These foams which are taught to be stable for periods of from 10 to 30 minutes are generated from a concentrate which is passed through a garden hose having a minimum water pressure of at least 15 psi. The concentrate is composed of (a) a foaming agent selected from water soluble salts of lauryl ether sulfate, water soluble salts of lauryl sulfonates, fatty acid esters of sodium isetheonate and mixtures thereof; (b) a foam enhancer selected from a specified group of compounds; (c) a foam stabilizer selected from a specified group of glycols and alcohols; (d) a foam-providing composition fluidity modifier selected from a specified group of alcohols; and (e) a plant agent such as a herbicide or insecticide.

U.S. No. 4,086,331 discloses gelatin-based foam compositions which may be applied as a protective covering. These foams composed of gelatin, anionic surface active agent, and a water soluble ferrous salt are relatively long lasting. These foams are very sensitive to temperature changes.

The use of whey solids as agricultural foam stabilizers is addressed in Lambou et al, "Whey Solids as Agricultural Foam Stabilizers", J. Agr. Food Chem., Vol. 21, No. 2, 1973. The foams disclosed therein persisted for a minimum of 6 hours.

However, long lasting foams do not completely resolve the problem of wind drift. In fact, the foams themselves will be subject to drifting. McCall et al evaluated several low expansion foams as possible carriers for herbicides in their work reported in "Influence of Foam Adjuvants on Activity of Selected Herbicides", WEED SCIENCE, Vol. 22, Issue 4 (July), 1974. The foam adjuvants used in this study were (1) alpha-(p-alkylphenyl)-omega-hydroxypoly(oxyethylene) sulfate; (2) a mixture of alpha-alkyl-omega-hydroxypoly(oxyethylene)sulfate, 1,3-propanediol and coconut fatty acid; and (3) a mixture of alcohol sulfates, salts of alkyl and dialkyl 2,4-diketotetra-hydrofuran, alkyl sulfonates and isopropanol.

SUMMARY OF THE INVENTION

It is an object of the present invention to provide low expansion foam compositions in which a herbicide or insecticide are incorporated.

It is also an object of the present invention to provide non-aerosol pesticidal or herbicidal foam compositions which are characterized by their rapid systemic absorption by the plant to which they have been applied.

It is yet another object of the present invention to provide a process for treating plant life such as trees with a herbicide or pesticide in which the problem of wind drift is avoided by utilizing such rapidly absorbed foam compositions.

These and other objects which will be apparent to those skilled in the art are accomplished by generating a foam from a concentrate composed of an alcohol, an emulsifier, water and a herbicide or a pesticide.

DETAILED DESCRIPTION OF THE INVENTION

The present invention relates to low expansion rapidly absorbed pesticidal or herbicidal foams, a process for their production and the use of those foams in treating plant life, particularly trees. More specifically, a concentrate composed of an alcohol, an emulsifier which is a liquid modified coconut acid or a surfactant blend of nonionic and anionic surfactants and water is formed. To this concentrate is added a pesticide or herbicide and the resulting mixture is thoroughly stirred. Pesticides and herbicides which are suitable for use in the present invention are generally in powder form. It may, therefore be advantageous to combine the pesticide or herbicide with a dispersing agent. Depending upon the concentration of the herbicide or pesticide in the resultant mixture, the mixture may be further diluted when it is ready for use or if dilution is unnecessary, the mixture may be placed in a spray apparatus. The foam forms when the mixture is pumped through the spraying apparatus. The foam generated upon spraying sticks to the surface of the plant for a period of from 30 seconds to about 3 minutes.

Alcohols which may be used to produce the concentrates of the present invention include isopropyl alcohol, ethyl alcohol and methyl alcohol. Isopropyl alcohol is particularly preferred. The alcohol is generally present in the concentrate in an amount of from 5 to 30 percent, preferably from 5 to 20 percent by weight of concentrate.

The emulsifiers suitable for use in the foam concentrate include liquid modified coconut acids and the specific blend of anionic and nonionic surfactants commercially available from Witco Chemical Corp. under the name Adsee AK31-73. Modified cocodiethanolamides such as those described in U.S. Pat. No. 4,176,176 are particularly preferred. The emulsifier is generally present in the foam concentrate in an amount of from 2 to 10 percent, preferably from 4 to 6 percent by weight.

The water used to form the concentrate is preferably distilled water but such high purity water is not generally necessary. The water may be present in the concentrate in an amount of from 70 to 95 percent, preferably from 75 to 90 percent by weight if the concentrate will be used without further dilution after the herbicide or pesticide has been added. If the concentrate to which herbicide or pesticide has been added will be further diluted prior to use, the water content of the concentrate may be substantially reduced. However, the water content must be high enough to form a solution when the herbicidal or pesticidal powder is added.

Herbicides suitable for use in the practice of the present invention include any of the known systemic herbicides. A specific example of such a herbicide is beta-(cyclohexyl-methylene)-alpha-(1,1-dimethylethyl)-IH-1,2,4-triazole-1-ethanol. Pesticides suitable for use in the practice of the present invention include any of the known systemic pesticides. A specific example of such a pesticide is Ethyl 3-methyl-4-(methylthio)-phenyl-(1-methylethyl)-phosphoroamidate. The herbicide or pesticide is generally present in an amount of from 2.5 to 25 percent, preferably from 3 to 10 percent by weight of the foam applied to the plant life. The optimum amount will of course depend upon the specific herbicide or pesticide being used.

Optional ingredients which may be included in the foam forming mixture include dispersing agents such as sodium lauryl sulfate, ethyl alcohol and aromatic solvents. Such optional ingredients may be present in an amount of up to 35 percent of the herbicide or pesticide used.

Spraying apparatus suitable for applying the foam forming composition include any device capable of incorporating air or a similar gas into the foam forming mixture. One example of such a device is a spray pump of the type commonly used for spraying household cleaners.

The compositions of the present invention are particularly useful for treating plant life having large vertical surfaces such as these because the foam carried herbicide or pesticide is absorbed before it has a chance of being blown away or coming into contact with the ground. The problems of wind drift and ground water contamination experienced with the known foam formulations are thus avoided.

Having thus described my invention, the following examples are given as being illustrative thereof.

EXAMPLES

EXAMPLE 1

The following concentrates were used in the foam forming formulations exemplified below:

| CONCENTRATE | Isopropyl Alcohol | LT-7-565 | Distilled Water |
|---|---|---|---|
| A | 5% | 5% | 90% |
| B | 10% | 5% | 85% |
| C | 15% | 5% | 80% |

LT-7-565 is a modified cocodiethanolamide available from Costec, Inc.

3.6% by weight of beta-(cyclohexylmethylene)-alpha-(1,1-dimethylethyl)-IH-1,2,4-triazole-1-ethanol was combined with 96.4% by weight of each of concentrates A, B and C. After being thoroughly mixed, each of the foam forming mixtures was placed in a pump spray apparatus and then applied to a wood surface and to tree branches. The foam generated from concentrate B was the most stable foam on both surfaces. Every foam was absorbed by the wood surface within one minute. Every foam was also absorbed by the tree branches within one minute. The foam generated from concentrate C ran about 2-3 inches down the vertical surface before being completely absorbed.

Example 2

20% by weight of Ethyl 3-methyl-4-(methylthio)phenyl (1-methylethyl) phosphoramidate (C.A.) and 80% by weight of concentrate composed of 5% sodium lauryl sulfate, 25% ethanol, 5% Adsee AK 31-73 surfactant blend and 45% water were mixed and then applied to a wood surface with a foam sprayer. A stable foam which did not stream down the surface was generated.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A foam composition formed from an alcohol, a modified cocodiethanolamide, water and a compound selected from systemic herbicides and systemic pesticides.

2. The composition of claim 1 in which the alcohol is isopropyl alcohol or ethyl alcohol.

3. The composition of claim 1 in which the herbicide or pesticide is present in an amount of from 2.5 to 25 percent by weight of the total foam composition.

4. The composition of claim 1 in which the alcohol is isopropyl alcohol and the modified coconut acid is a modified cocodiethanolamide.

5. The composition of claim 4 in which the isopropyl alcohol is present in an amount of from 5 to 15 percent by weight of the total alcohol, modified cocodiethanolamide and water and the modified cocodiethanolamide is present in an amount of from 3 to 6 percent of the mixture of isopropyl alcohol, modified cocodiethanolamide and water.

* * * * *